(12) United States Patent
Giersch et al.

(10) Patent No.: US 9,345,524 B2
(45) Date of Patent: May 24, 2016

(54) ULTRASONIC APPLICATOR

(75) Inventors: Helge Giersch, Kiel (DE); Klaus Dorawa, Safnern (CH)

(73) Assignee: Stryker European Holdings I, LLC, Kalamazoo, MI (US)

(*) Notice: Subject to any disclaimer, the term of this patent is extended or adjusted under 35 U.S.C. 154(b) by 1006 days.

(21) Appl. No.: 13/079,913

(22) Filed: Apr. 5, 2011

(65) Prior Publication Data
US 2011/0251600 A1   Oct. 13, 2011

(30) Foreign Application Priority Data

Apr. 8, 2010 (EP) .................................... 10159348

(51) Int. Cl.
| | |
|---|---|
| A61B 17/00 | (2006.01) |
| A61B 17/86 | (2006.01) |
| A61B 17/70 | (2006.01) |
| A61B 17/88 | (2006.01) |

(52) U.S. Cl.
CPC ........... *A61B 17/864* (2013.01); *A61B 17/7098* (2013.01); *A61B 17/8822* (2013.01)

(58) Field of Classification Search
CPC ............. A61B 17/885; A61B 17/8875; A61B 2017/00106; A61B 2017/0011; A61B 2017/22004; A61B 2017/22012; A61B 2017/22014; A61B 18/0206
USPC ...................... 411/171; 433/86, 89, 119, 164; 606/86 R, 99, 104, 300, 319, 326, 329, 606/331
See application file for complete search history.

(56) References Cited

U.S. PATENT DOCUMENTS

| | | | |
|---|---|---|---|
| 4,653,489 | A | 3/1987 | Tronzo |
| 5,944,737 | A | 8/1999 | Tsonton et al. |
| 6,110,178 | A | 8/2000 | Zech et al. |
| 6,921,264 | B2 | 7/2005 | Mayer et al. |
| 7,008,226 | B2 | 3/2006 | Mayer et al. |
| 7,163,542 | B2 | 1/2007 | Ryan |
| 7,335,205 | B2 | 2/2008 | Aeschlimann et al. |
| 2005/0222571 | A1* | 10/2005 | Ryan .............................. 606/80 |
| 2007/0063618 | A1 | 3/2007 | Bromfield |
| 2008/0109007 | A1 | 5/2008 | Schwager et al. |
| 2008/0243151 | A1* | 10/2008 | Binmoeller et al. .......... 606/153 |
| 2009/0018471 | A1* | 1/2009 | Dorawa et al. .................... 601/2 |
| 2009/0018590 | A1 | 1/2009 | Dorawa et al. |
| 2010/0211111 | A1 | 8/2010 | Sonntag et al. |

FOREIGN PATENT DOCUMENTS

| | | |
|---|---|---|
| EP | 2014248 A1 | 1/2009 |
| JP | 2000513985 A | 10/2000 |
| WO | 2009046126 A1 | 4/2009 |

OTHER PUBLICATIONS

Partial European Search Report, EP 10 159 348.1, dated Oct. 15, 2010.

* cited by examiner

*Primary Examiner* — Todd E Manahan
*Assistant Examiner* — Jessica Weiss
(74) *Attorney, Agent, or Firm* — Lerner, David, Littenberg, Krumholz & Mentlik, LLP

(57) ABSTRACT

An ultrasonic applicator includes an ultrasonic converter accommodated within a converter housing, a first housing, and a second housing. A rear end portion of the first housing is located in the second housing and an inner end portion of the converter housing is located in the rear end portion of the first housing. A length of the rear end portion of the first housing is adjustable. An outer end portion of the converter housing is connected with the second housing via an elastic element, so that a restoring force may be applied on the converter housing by virtue of a movement of the converter housing relative to the second housing.

19 Claims, 7 Drawing Sheets

ULTRASONIC APPLICATOR

CROSS-REFERENCE TO RELATED APPLICATION

The present application claims priority from European Patent Application No. EP 10 159 348.1 filed Apr. 8, 2010, which is incorporated herein by reference.

BACKGROUND OF THE INVENTION

The invention in general relates to sonic fusion technology. In particular, the invention relates to an ultrasonic applicator as well as to a method of using the same. An exemplary use of an ultrasonic applicator according to the invention may be for augmenting a bone screw within a fractured bone.

U.S. Pat. No. 4,653,489 discloses a system wherein a fixation cement is introduced through a bone screw into a portion of a bone afflicted by osteoporosis. Femoral neck fractures as well as distal femoral fractures can be fixated by means of this system.

US 2007/0063618 discloses an ultrasonic transducer device, comprising an active piezo ceramic material that contains less than 2% lead, piezo materials with a low Curie temperature, a high compressive bias force applied to the piezo ceramic elements, a bias bold sub-assembly that includes a component assembled with a low-temperature glass-transition point filled epoxy material, and/or a permanently attached end effector with a self-locking taper.

The system in accordance with the prior art comprises a bone screw having a flow cavity, that is an axial through bore through which bone cement can be introduced into the portion of the tip of the screw. The bone cement is advanced by a device which is releasably attached to the trailing end of the screw. This device is similar to a commercially available syringe in comprising substantially a cylindrical barrel and a plunger. The barrel forms a cavity in which the plunger is movable to and fro.

In use of this prior art device, the fixation cement is filled into the barrel, after which the plunger is urged against the cement. By applying manual compression force, the fixation cement is jetted into the axial through bore of the bone screw. Due to the pressure, the fixation cement is adequately fluidized so that it can pass through the proximal end of the bone screw into the bone, as a result of which the bone screw is augmented in the bone.

This system has the drawback that the manual pressure applied to the fixation cement varies, not only basically from application to application but also during the application itself, so that the distribution of the fixation cement within the portion of the bone and the tip of the bone screw is neither reliable nor even.

BRIEF SUMMARY OF THE INVENTION

An aspect of the invention is to provide a device and method by means of which a reliable and even augmentation of, for example, a bone screw at an implantation site in the bone can be assured.

In general, an ultrasonic applicator according to the invention comprises an ultrasonic converter accommodated in a converter housing, a first housing, and a second housing. A rear end portion of the first housing is located in the second housing and an inner end portion of the converter housing is located in the rear end portion of the first housing.

A length of the rear end portion of the first housing is adjustable, which means that the first housing can be moved into or out of the second housing, so that the overall length of the first and second housing is variable.

An outer end portion of the converter housing is connected with the second housing via an elastic element, so that a restoring force may apply on the converter housing by virtue of a movement of the converter housing relative to the second housing. This means, that for example by pulling the outer end portion of the converter housing out of the second housing, an elastic element will be tensioned which results in a restoring force being applied to the converter housing.

According to one aspect of the invention, the adjustment of the length of the rear end portion, which is located inside the second housing, is achieved by virtue of a rotation of the first housing relative to the second housing, wherein a thread formed in an outer surface of the first housing engages with at least a protrusion provided in the second housing.

According to another aspect of the invention, a depression is formed in an outer surface of the first housing, wherein a locking pin is arranged at the second housing, so that the locking pin is capable of engaging the depression. By way of this, an adjusted length of the first housing relative to the second housing may be locked by an engagement of the locking pin and the depression.

The locking pin may be biased in the direction of the depression, so that the locking pin will engage automatically with the depression, as soon as the locking pin is aligned with the depression.

According to another aspect of the invention, a thread is formed in an outer surface of the first housing and a depression is formed within the pitch of the thread. At the second housing, a locking pin is provided, which firstly is capable to engage within the pitch of the thread and secondly is capable to engage with the depression. In this case, an adjustment of the length of the housing can be achieved by rotating the first housing relative to the second housing, wherein the locking pin will additionally engage with the depression, as soon as the locking pin is aligned with the depression located within the pitch of the thread.

It is noted, that also a plurality of depressions may be provided within the pitch of the thread (or outside of the pitch of the thread), so that the length of the first and second housing may be adjusted and locked in a pre-determined way, for example in periodic distances.

According to another aspect of the invention, a recess is formed in an outer surface of the converter housing, wherein a retainer is arranged at the second housing, so that the retainer is capable of engaging the recess, when the converter housing is in a position providing a restoring force of the elastic element. By way of the retainer, it is possible to provide for a rest position with tensioned elastic element.

The retainer may be biased in the direction of the recess, and a trigger may be provided for moving the retainer away from the recess. Thus, by pulling the outer end portion of the converter housing out of the second housing, the elastic element will be tensioned and the biased retainer will engage with the recess in the converter housing. An operator may pull the trigger so that the retainer is moved out of the recess and the tension force of the elastic element will urge the converter housing together with the ultrasonic converter in the direction of the front end portion of the first housing, which may cause a sonotrode tip at the ultrasonic converter to move out of the front end portion of the first housing.

As soon as the ultrasonic converter is activated, the biased tip of the sonotrode of the ultrasonic converter may be capable of fluidizing a polymer pin located in a bone screw attached at the front end portion of the first housing, so that the fluidized polymer material may be pressed out of the bone screw and into bone cavities, for augmenting the bone screw within the bone.

To provide for a better handling of the ultrasonic applicator, a grip portion at the second housing is provided in accordance with another embodiment of the invention.

It will be understood, that a tissue protection sleeve, which is a kind of a lengthening piece, may be arranged between the front end of the first housing and a bone screw.

To adapt the ultrasonic applicator to bone screws having a different length, the first housing is adjustable relative to the second housing and therefore, the overall length of the first and second housing of the ultrasonic applicator is adjustable. This leads to the effect that the tip of the ultrasonic converter will move more or less out of the housing. By way of this, it can be assured that, independently from the length of the actually utilized bone screw, a predefined amount of a polymer material will be fluidized by a predefined pressure together with ultrasonic vibrations, so that a reliable and even augmentation of a bone screw at an implantation site can be achieved.

Various aspects of the invention are achieved by an ultrasonic applicator, comprising an ultrasonic converter, accommodated in a converter housing. The converter housing has an inner end portion and an outer end portion. A first housing is also provided having a front end portion and a rear end portion. The inner end portion of the converter housing is located in the rear end portion of the first housing. A second housing is provided that at least partially surrounds the first housing. The rear end portion of the first housing is located in the second housing. A length of the rear end portion of the first housing is adjustable. An elastic element is arranged between the outer end portion of the converter housing and the second housing, so that a restoring force may apply on the converter housing by virtue of a movement of the converter housing relative to the second housing to a biased position.

A recess is formed in an outer surface of the converter housing, wherein a retainer is arranged at the second housing, so that the retainer is capable of engaging the recess when the converter housing is in the biased position. The retainer is biased in the direction towards the converter housing. A trigger is provided for moving the retainer away from the first housing. A thread is formed in an outer surface of the first housing, so that the length of the rear end portion, located in the second housing, is adjustable by virtue of a rotation of the first housing relative to the second housing. A depression is formed in an outer surface of the first housing, wherein a locking pin is arranged at the second housing, so that the locking pin is capable of engaging the depression. The locking pin is biased in the direction to the first housing. A switch element is provided for blocking or releasing the locking pin. The ultrasonic applicator further comprises a grip at the second housing. The front end portion of the first housing comprises a through bore for a tip of the ultrasonic converter and a coupling element for a connection of the first housing with a tissue protection sleeve or a bone screw. An indicator is provided at an outer surface of the first housing, and wherein the second housing further comprises a viewing window, wherein the indicator is visible in the viewing window when the first housing is arranged in a determined position relative to the second housing.

A method for using the ultrasonic applicator includes adjusting the position of the first housing relative to the second housing, pulling the outer end portion of the converter housing out of the second housing to tension the elastic element between the converter housing and the second housing. The method includes activating the ultrasonic converter, and applying pressure together with ultrasonic vibrations to an object at the tip of the sonotrode of the ultrasonic converter. The method further comprises retaining the converter housing relative to the second housing in a position in which the elastic element is tensioned, releasing the converter housing after the ultrasonic converter is activated.

Various aspects are provided by an ultrasonic applicator having a first housing having front and rear end portions, an ultrasonic converter housing having first and second ends moveably mounted in the first housing and an ultrasonic converter mounted with the ultrasonic converter housing. A second housing at least partially surrounds the first housing and is axially adjustably mounted on the first housing. A locking element is provided for locking the relative axial position of the first and second housing. An elastic element extends between the ultrasonic converter housing and the second housing with the elastic element being put under tension on axial movement of the converter housing with respect to the second housing in a direction away from the first housing.

The aspects defined above and further aspects, features and advantages of the present invention can also be derived from the examples of the embodiments to be described hereinafter and are explained with reference to examples of embodiments to which the invention is not limited.

BRIEF DESCRIPTION OF THE DRAWINGS

The invention will now be detailed by way of an exemplary embodiment with references to the attached drawings.

It is noted that the illustration in the drawings is only schematically and not to scale. In different figures, similar elements are provided with the same reference signs.

DETAILED DESCRIPTION

Figure 1:
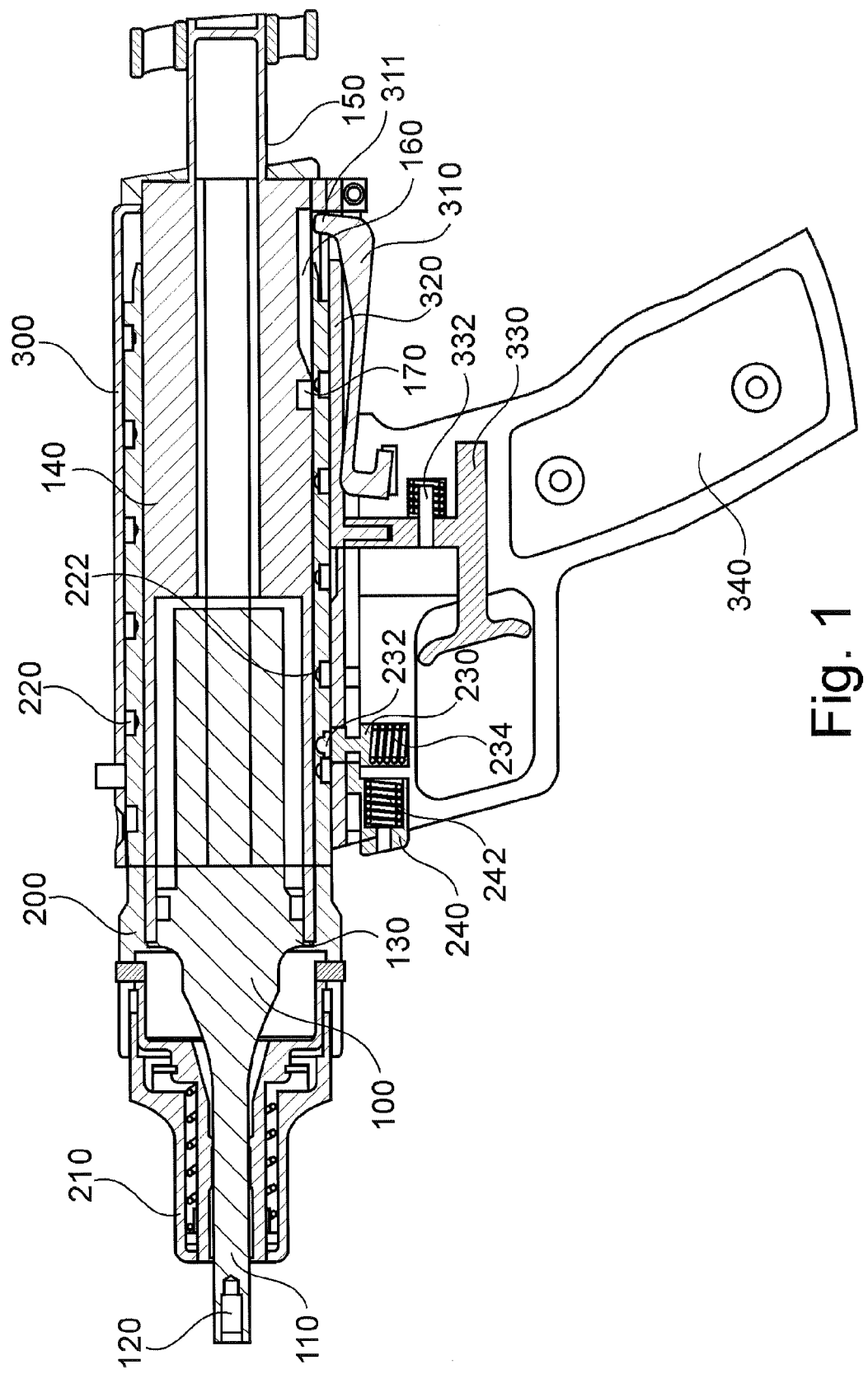
FIG. 1 is a cross-sectional side view of an ultrasonic applicator according to the invention.

Referring to FIG. 1 there is shown a sectional side view of an ultrasonic applicator according to the invention. The ultrasonic applicator comprises an ultrasonic converter 100, a converter housing 140, a first housing 200 and a second housing 300.

The ultrasonic converter 100 includes a tip portion 110 with a threaded bore 120 for a connection with a sonotrode. Further, the converter 100 is located inside the converter housing 140 and is fixed to the converter housing at the relatively small portion 130. A main part of converter 100, apart from the portion 130, is thus out of contact with any housing, so that vibrations caused by ultrasonic converter 100 may be transmitted to housing 140 in a reduced way.

The converter housing 140 is substantially located within first housing 200, wherein a rear end portion 150 of converter housing 140 extends out of second housing 300. The converter housing includes an opening to the outside so that for example a cable (not shown) may be provided for supplying energy to the ultrasonic converter.

The first housing 200 includes a front end portion 210 which may be formed to mate with a proximal end of a tissue protection sleeve or a bone screw. The first housing 200 further includes a thread 220 forming a substantially spiral groove in an outer surface of the first housing. Within the thread 220 a plurality of depressions 222 are provided in regular distances.

For an engagement with the thread 220 as well as the depressions 222, a locking pin 230 is provided at the second housing 300. The locking pin 230 comprises a substantially spherical tip portion, adapted to engage with a depression 222. Further, the locking pin 230 is biased by an elastic element 234 urging the locking pin in the direction to the first housing 200 and into a depression 222, in case the locking pin is aligned with such a depression.

A switch element 240 is provided which is biased by another elastic element 242. According to this embodiment, the switch element 240 may block a movement of the locking pin 230 in case the locking pin engages a depression 222. Pressing the switch element 240 will result in releasing the locking pin so that the tip 232 of the locking pin may move out of a depression 222 and a rotation of the first housing 200 relative to the second housing 300 may be possible. By way of such a rotation, the overall length of the first and second housing may be adjusted.

For example, every 5 mm in a longitudinal direction, a depression 222 may be provided, so that by virtue of rotating the first housing 200 in steps of about 90 degree, the overall length of the first and second housing may be locked every 5 mm.

Also shown in FIG. 1, a retainer 310 is provided at the second housing 300. The retainer 310 is movable by a movement of a trigger 330 which is biased by a further elastic element 332. A movement of the trigger 330 will be transmitted by an element 320 to the retainer 310, moving the retainer away from the converter housing 140.

In the converter housing 140, a slot-like recess 160 as well as a recess 170 is provided. The slot-like recess 160 is formed so that an end 311 of the retainer 310 is capable of engaging with the slot-like recess, as long as the converter housing is not pulled out of the second housing 300. End 311 of the retainer 310 will engage with the recess 170, as soon as the converter housing 140 is pulled out of the second housing 300, tensioning the elastic elements arranged between the converter housing 140 and the second housing 300.

Figure 2:
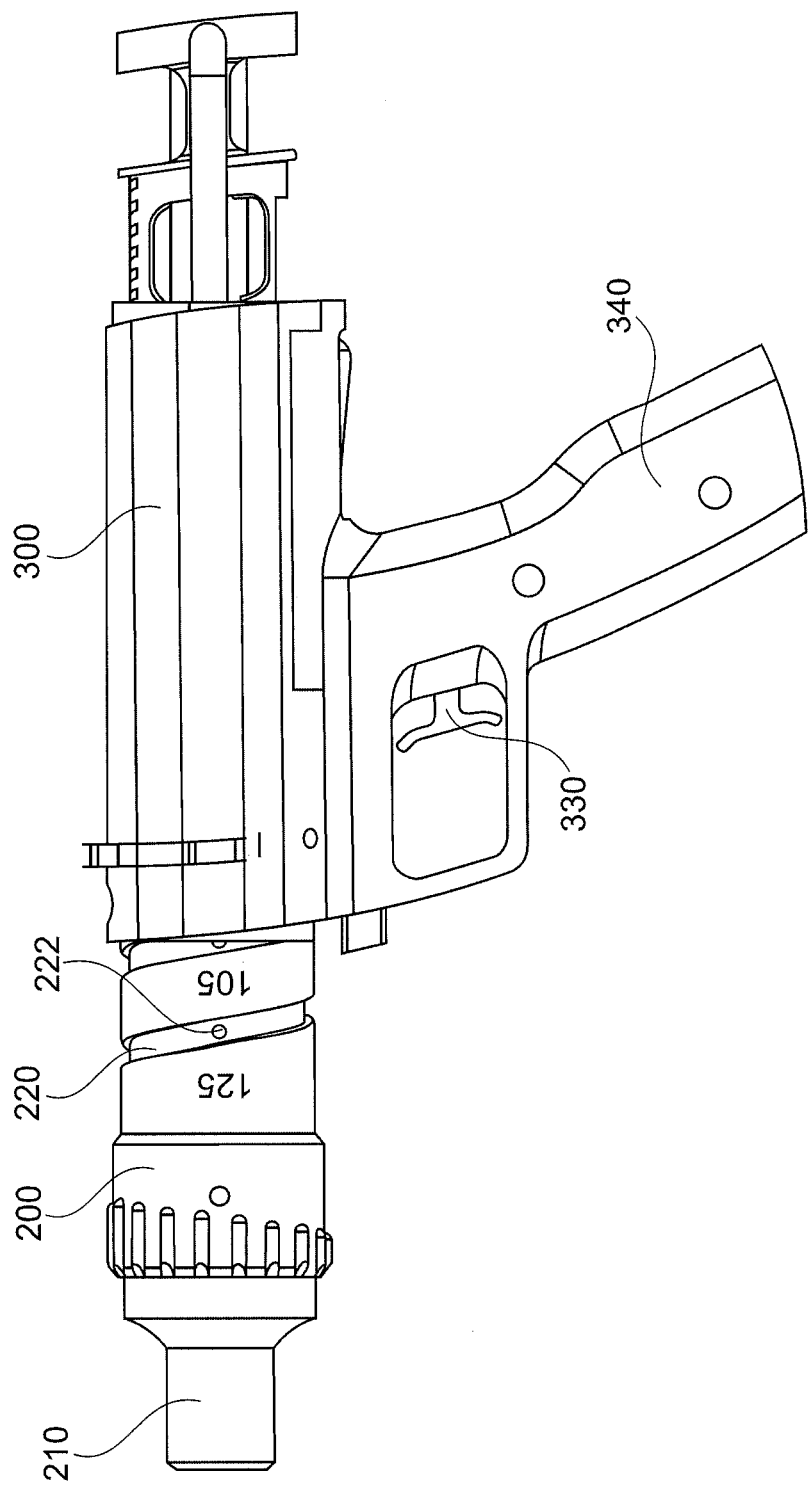
FIG. 2 is a side view of an ultrasonic applicator in accordance with the invention.

As can also be seen in FIG. 2, the second housing 300 is provided with a grip portion 340, wherein the trigger 330 is arranged, so that the trigger may be easily pulled by an index finger of a hand while holding the grip. Further shown in FIG. 2 is the location of a depression 222 within the pitch of the thread 220 of the first housing 200.

Figure 3:
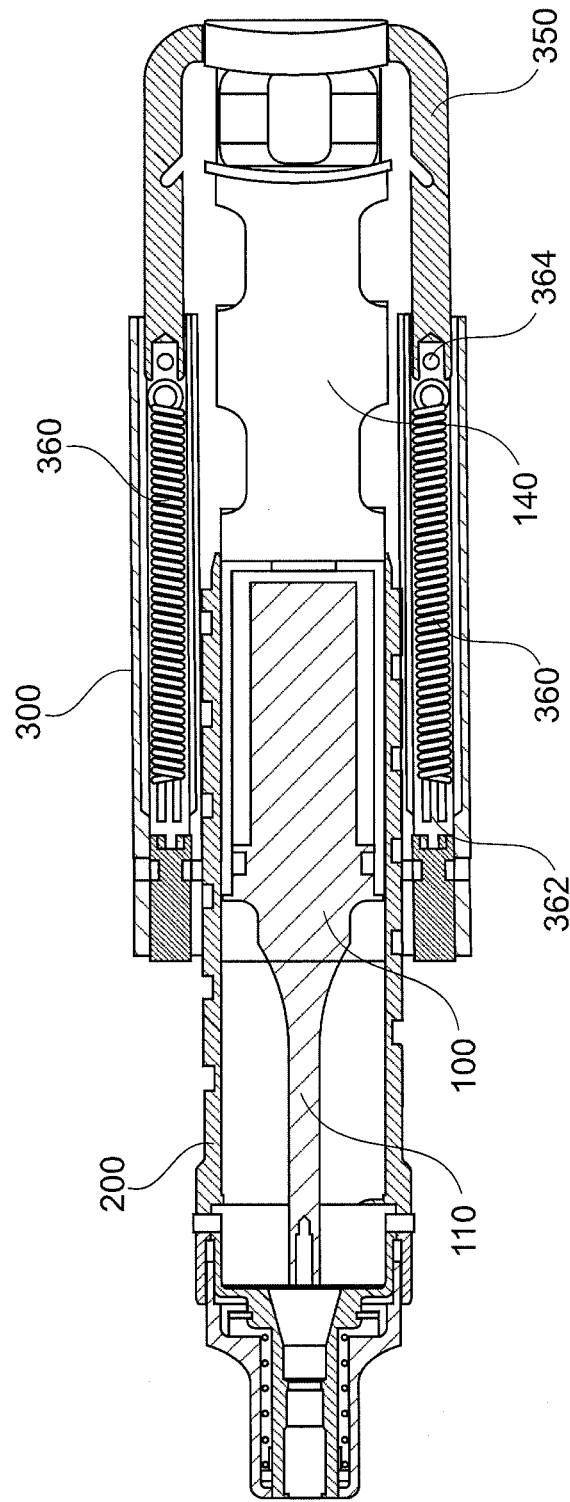
FIG. 3 is a cross-sectional top view of the ultrasonic applicator according to the invention.

A further sectional view of the ultrasonic applicator according to the invention is shown in FIG. 3. This sectional view is a top view showing the first housing 200, the second housing 300 as well as the ultrasonic converter 100 within the converter housing 140. Within the second housing 300, two elastic elements, that is tension springs 360 are located. Each of the elastic elements 360 is connected with the second housing 300 at a point 362, and is connected with the converter housing 140 via a strap 350 at the point 364. Therefore, pulling rear end portion 150 of the converter housing 140 out of the second housing 300 will tension the elastic elements 360.

Figure 4:
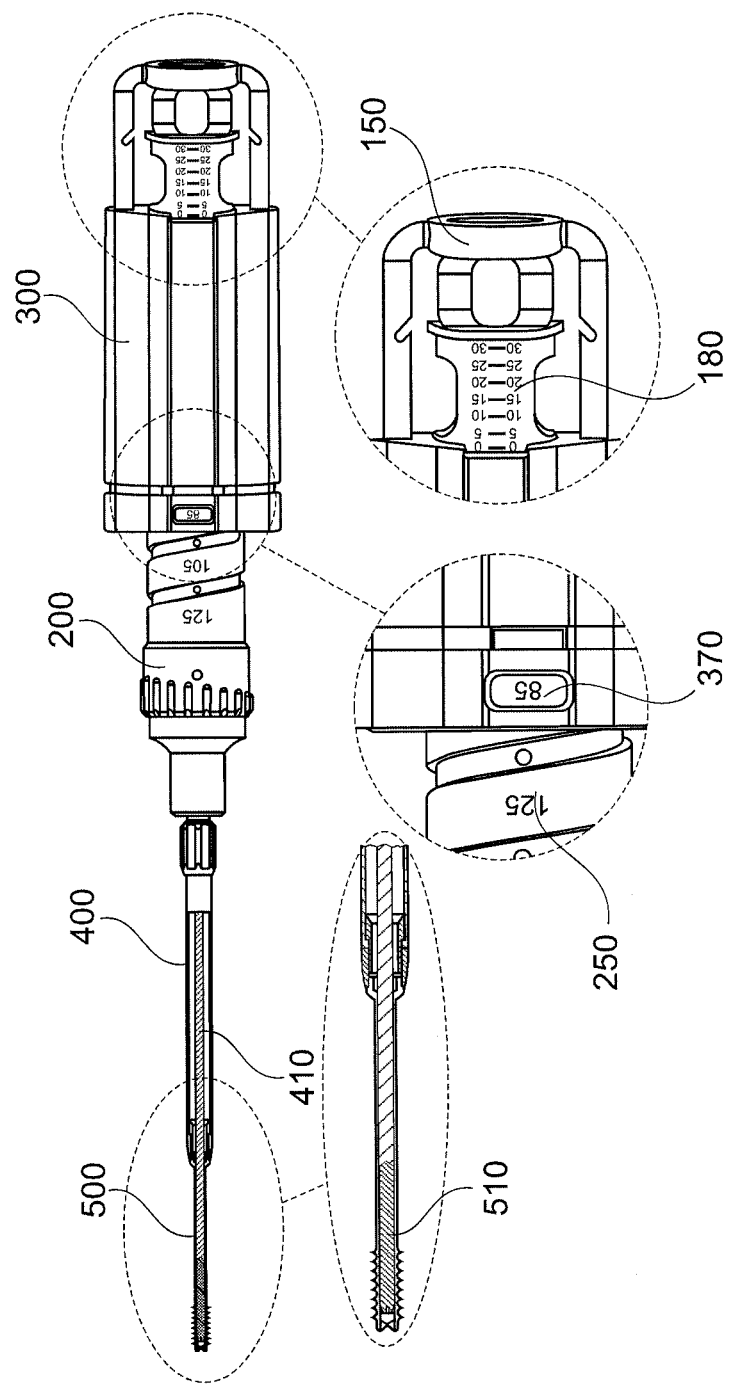
FIGS. 4 and 5 show examples of ultrasonic applicators with different adjusted overall length of the first and second housing of the ultrasonic applicator.
Figure 5:
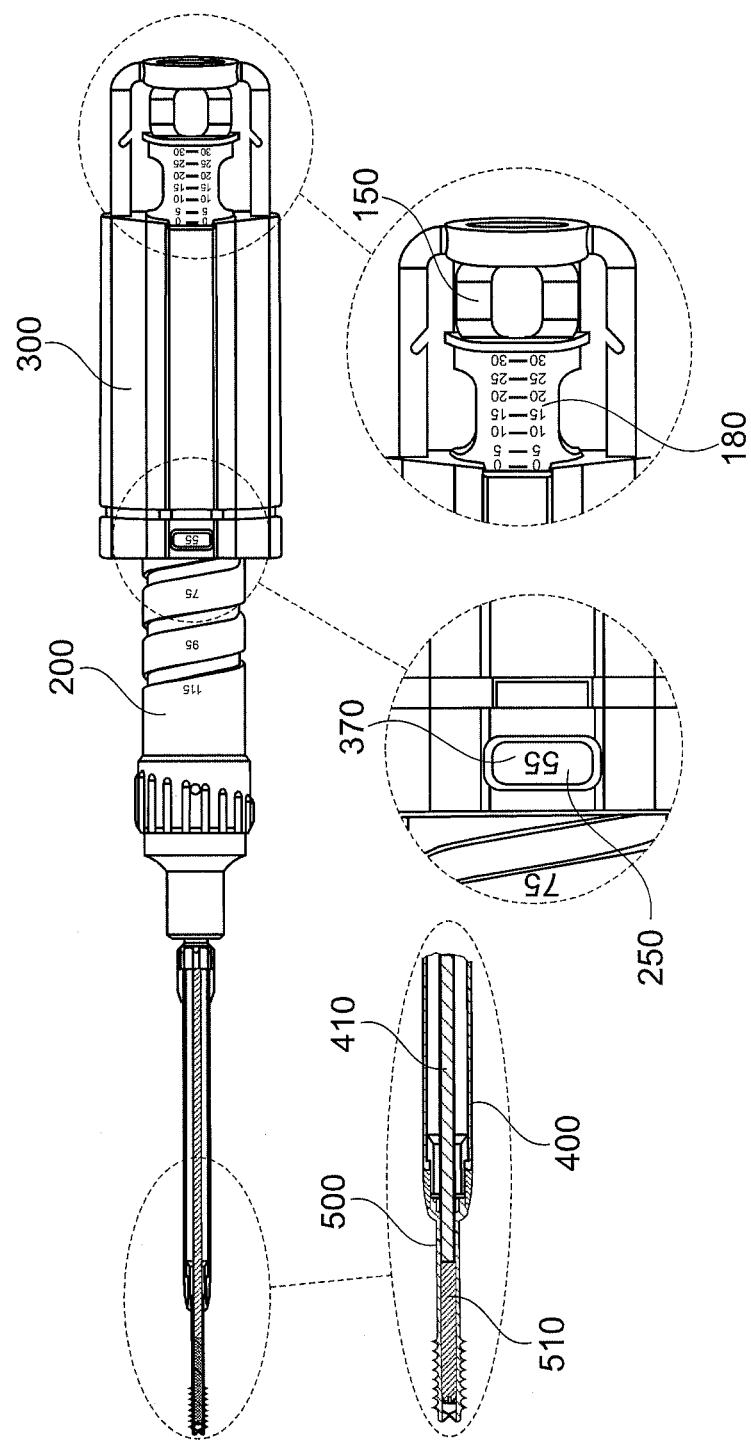
Figure 6:
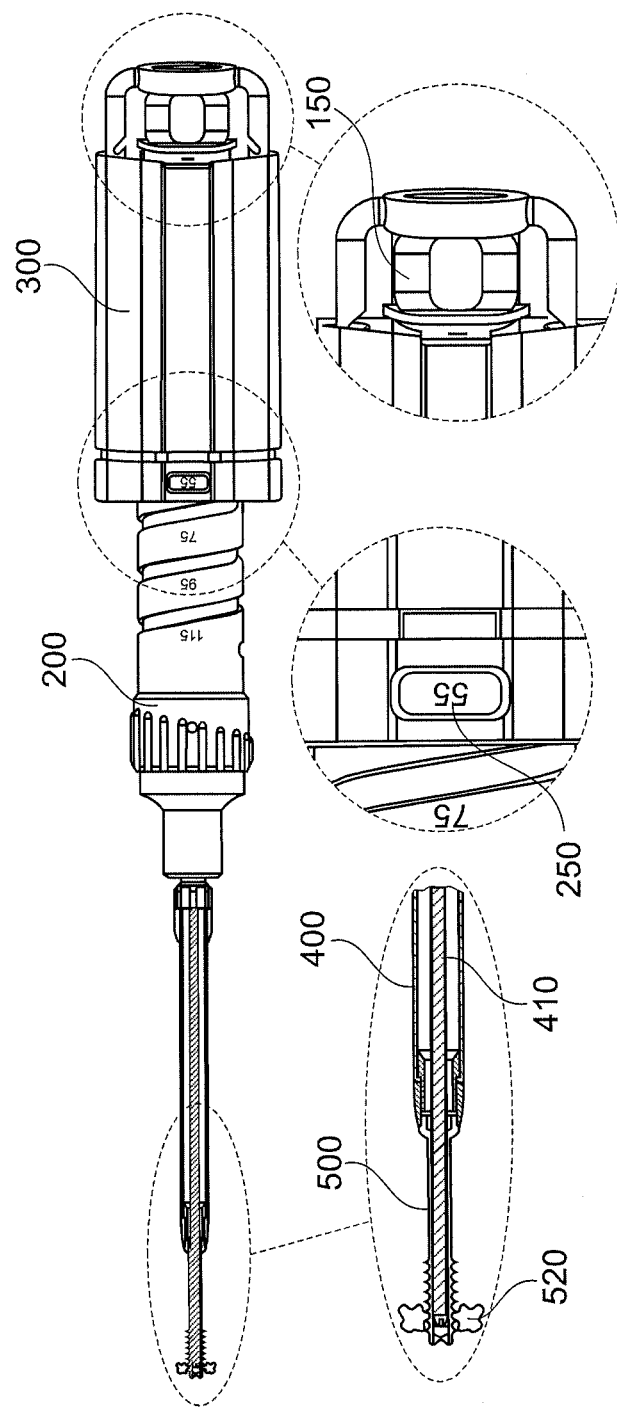
FIG. 6 illustrates an ultrasonic applicator, with the outer end portion of the converter housing moved back into the second housing, so that polymer material is pressed out of a bone screw.

In FIGS. 4, 5, and 6, examples for an application of the ultrasonic applicator according to the invention is illustrated.

In FIG. 4, the ultrasonic applicator is used with a long screw 500, wherein a tissue protection sleeve 400 is arranged between the screw 500 and the front end of the first housing 200. Between the tip of the ultrasonic converter and a polymer pin 510 within the screw 500, an ultrasonic sonotrode 410 is provided. Here, outer end portion 150 of converter housing 140 is pulled out of the second housing 300, so that a scale 180 is visible which indicates an amount of polymer material to be fluidized and to be pressed out of the screw 500.

To facilitate the adjustment of the first housing 200 relative to the second housing 300, signs, for example numbers 250 are provided at the outer surface of the first housing 200, and a viewing window 370 is provided in the second housing 300. The numbers 250 at the first housing 200 may be chosen corresponding to the length of a used screw 500. In the example of FIG. 4, the number 85 visible in the window 370 indicates, that the length of the screw 500 is 85 mm. It may be understood, that any kind of sign may be suitable to indicate a relation between the length of the housing and a screw having a particular length.

In the example of FIG. 5, the first housing 200 is adjusted relative to the second housing 300, so that the number 55 is visible within the window 370. Accordingly, the sonotrode 410 extends less far out of the tissue protection sleeve 400 and thus less into the shorter screw 500. Further, the outer end portion 150 of the converter housing is pulled out of the second housing 300, so that the scale 180 is visible, and the elastic elements in the second housing are biased.

In FIG. 6, a situation is shown, in which trigger 330 has been pulled, and therefore, the tension force of elastic elements 360 inside the second housing 300 has already pressed polymer material 520 out of the bone screw. By moving the outer end portion 150 back into the second housing 300, the sonotrode 410 is pushed further into the bone screw 500. In this example, a bone screw 500 with a length of 55 mm is utilized.

Figure 7:
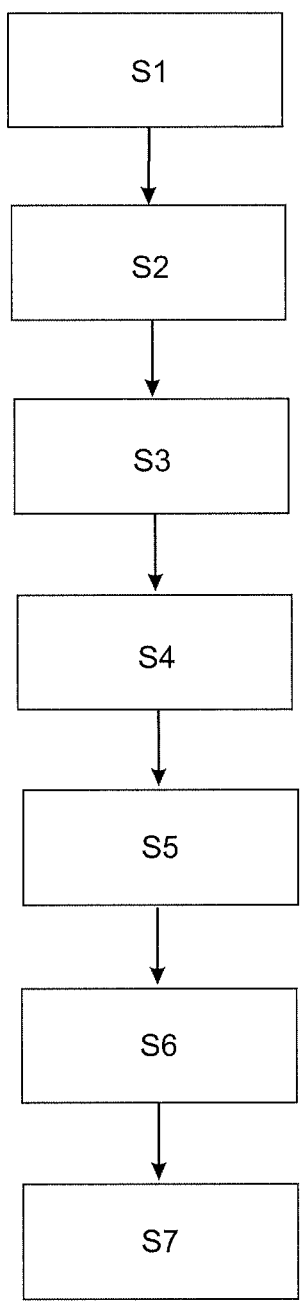
FIG. 7 is a flow-chart illustrating a method according to the invention.

The flow-chart in FIG. 7 illustrates the principle of using an ultrasonic applicator according to the invention. It will be understood that the steps described with respect to the method are major steps, wherein these major steps might be differentiated or divided into several sub-steps. Furthermore, there might be also sub-steps between these major steps. Therefore, a sub-step is only mentioned if that step may be important for the understanding of the principles of the method according to the invention.

In step S1, the position of first housing 200 relative to second housing 300 is adjusted. This may be achieved by rotating first housing 200 relative to second housing 300 so that locking pin 230 follows the helical thread pitch 220 provided in the first housing.

In step S2, the overall length of—the first and second housing is locked by an engagement of the locking pin 230 in a depression 222 of the first housing. At this, a number 250 may be visible within the viewing window 370 in second housing 300, wherein the number may correspond to a length of a screw currently used with the ultrasonic applicator.

In step S3, the outer end portion 150 of the converter housing 140 is pulled out of the second housing, thereby tensioning the elastic element 360 between converter housing 140 and second housing 300.

In step S4 a movement of the converter housing 140 relative to the second housing 300 is blocked in a position in which the elastic element 360 is tensioned, by an engagement of retainer 310 on the second housing with a corresponding recess 160 provided in the converter housing 140.

In step S5, the ultrasonic converter is activated.

In step S6, the converter housing 140 is released, by pulling a trigger and thus moving the retainer out of the recess.

Finally, in step S7, pressure together with ultrasonic vibration is applied to an object at the tip of the sonotrode of the ultrasonic converter, wherein the object may be a polymer pin which is located within a bone screw, so that the polymer material of the polymer pin is fluidized and simultaneously pressed out of the screw at the distal portion of the screw.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements, and indefinite article "a" or "an" does not exclude a plurality. The mere fact that the certain measures are recited in mutually different dependent claims does not indicate that a combination of these measures cannot be used to advantage. Any reference signs in the claims should not be construed as limiting the scope.

The invention claimed is:

1. An ultrasonic applicator, comprising:
   an ultrasonic converter, accommodated in a converter housing having an inner end portion and an outer end portion,
   a first housing having a front end portion and a rear end portion,
   wherein the inner end portion of the converter housing is located in the rear end portion of the first housing,
   a second housing at least partially surrounding the first housing,
   wherein the rear end portion of the first housing is located in the second housing, wherein a length of the rear end portion is adjustable,
   wherein an elastic element is arranged between the outer end portion of the converter housing and the second housing, so that a restoring force may apply on the converter housing by virtue of a movement of the converter housing in an axial direction relative to the second housing to a biased position, and
   wherein a recess is formed in an outer surface of the converter housing, and a biased retainer is arranged at the second housing, so that the retainer is biased into engagement with the recess by moving in a transverse direction to the axial direction to hold the converter housing relative to the second housing when the converter housing is in the biased position.

2. The ultrasonic applicator according to claim 1, wherein a trigger is provided for moving the retainer away from the first housing.

3. The ultrasonic applicator according to claim 1, wherein a thread is formed in an outer surface of the first housing, so that the length of the rear end portion, located in the second housing, is adjustable by virtue of a rotation of the first housing relative to the second housing.

4. The ultrasonic applicator according to claim 1, wherein a depression is formed in an outer surface of the first housing, wherein a locking pin is arranged at the second housing, so that the locking pin is capable of engaging the depression.

5. The ultrasonic applicator according to claim 4, wherein the locking pin is biased in the direction to the first housing.

6. The ultrasonic applicator according to claim 5, wherein a switch element is provided for blocking or releasing the locking pin.

7. The ultrasonic applicator according to claim 1, further comprising a grip at the second housing.

8. The ultrasonic applicator according to claim 1, wherein the front end portion of the first housing comprises a through bore for a tip of the ultrasonic converter and a coupling element for a connection of the first housing with a tissue protection sleeve or a bone screw.

9. The ultrasound applicator according to claim 1, wherein an indicator is provided at an outer surface of the first housing, and wherein the second housing further comprises a viewing window, wherein the indicator is visible in the viewing window when the first housing is arranged in a determined position relative to the second housing.

10. A method for using the ultrasonic applicator according to claim 1, the method comprising:
    adjusting the position of the first housing relative to the second housing,
    pulling the outer end portion of the converter housing in a first direction out of the second housing, to tension the elastic element between the converter housing and the second housing,
    moving a retainer in a second direction transverse to the first direction into a recess formed in the outer surface of the converter housing, to retain the converter housing relative to the second housing in a position in which the elastic element is tensioned,
    activating the ultrasonic converter, and releasing the converter housing by moving the retainer in the second direction out of the recess, and
    applying pressure together with ultrasonic vibrations to an object at the tip of the sonotrode of the ultrasonic converter.

11. An ultrasonic applicator comprising:
    a first housing having front and rear end portions,
    an ultrasonic converter housing having first and second ends moveably mounted in the first housing,
    an ultrasonic converter mounted within the ultrasonic converter housing;
    a second housing at least partially surrounding and axially adjustably mounted on the first housing,
    a locking element for locking the relative axial position of the first and second housings; and
    an elastic element extending between the ultrasonic converter housing and the second housing, the elastic element put under tension on axial movement of the converter housing with respect to the second housing in a direction away from the first housing;
    a lateral recess formed in an outer surface of the converter housing; and
    a retainer arranged at the second housing and being capable of engaging the lateral recess, when the converter housing is moved axially with respect to the second housing;
    wherein the retainer is biased in the direction transverse to the axial direction and towards the converter housing.

12. The ultrasonic applicator according to claim 11, wherein a trigger is provided for moving the retainer away from the first housing.

13. The ultrasonic applicator according to claim 12, wherein a thread is formed in an outer surface of the first housing, so that the length of the rear end portion thereof, located in the second housing, is adjustable by virtue of a rotation of the first housing relative to the second housing.

14. The ultrasonic applicator according to claim 11, wherein a depression is formed in an outer surface of the first housing, wherein a locking pin is arranged on the second housing, so that the locking pin is capable of engaging the depression.

15. The ultrasonic applicator according to claim 11, wherein the front end portion of the first housing comprises a through bore for a tip of the ultrasonic converter and a coupling element for a connection of the first housing with a tissue protection sleeve or a bone screw.

16. The ultrasound applicator according to claim 11, wherein an indicator is provided at an outer surface of the first housing, and wherein the second housing further comprises a viewing window, wherein the indicator is visible in the viewing window when the first housing is arranged in a first position relative to the second housing.

17. An ultrasonic applicator, comprising:
an ultrasonic converter, accommodated in a converter housing having an inner end portion and an outer end portion,
a first housing having a front end portion and a rear end portion,
wherein the inner end portion of the converter housing is located in the rear end portion of the first housing,
a second housing at least partially surrounding the first housing,
wherein the rear end portion of the first housing is located in the second housing, wherein a location of the rear end portion with respect to the first housing is adjustable,
wherein an elastic element is arranged between the outer end portion of the converter housing and the second housing, so that a restoring force may act on the converter housing along an axial direction by a movement of the converter housing relative to the second housing to a biased position,
wherein a recess is formed in an outer surface of the converter housing, wherein a retainer is arranged on the second housing and extends through the first housing, so that the retainer is moveable in a direction transverse to the axial direction towards and away from the converter housing to selectively engage and disengage the recess on the converter housing, and when engaged, to hold the converter housing in the biased position when the converter housing is moved relative to the second housing, the retainer being spring biased in the transverse direction into engagement with the recess in the converter housing.

18. The ultrasonic applicator as set forth in claim 17 further comprising a spring loaded actuator for disengaging disengaging the retainer from the recess in the converter housing.

19. The ultrasonic applicator as set forth in claim 17 wherein the spring loaded actuator for disengaging the retainer from the recess comprises a spring loaded trigger.

* * * * *